(12) United States Patent
Gonnen et al.

(10) Patent No.: US 9,763,626 B2
(45) Date of Patent: Sep. 19, 2017

(54) ACOUSTIC SPIROMETER SYSTEM (71) Applicant: MEYTAR (DITAL) ENGINEERING LIMITED, Netanya (IL)

(72) Inventors: Lior Gonnen, Tel-Aviv (IL); David Groberman, Even Yehuda (IL); David Solomon, Zichron Ya'akov (IL); Rahav Cohen, Raanana (IL)

(73) Assignee: BREATHE.ME LTD., Ra'Annana (IL)

( * ) Notice: Subject to any disclaimer, the term of this patent is extended or adjusted under 35 U.S.C. 154(b) by 3 days.

(21) Appl. No.: 15/147,699

(22) Filed: May 5, 2016

(65) Prior Publication Data

US 2016/0242701 A1 Aug. 25, 2016

Related U.S. Application Data (63) Continuation-in-part of application No. 13/825,146, filed as application No. PCT/IB2011/054141 on Sep. 21, 2011, now abandoned.

(Continued)

(51) Int. Cl.
*A61B 5/087* (2006.01)
*A61B 5/00* (2006.01)
*A61B 5/09* (2006.01)

(52) U.S. Cl.
CPC .......... *A61B 5/7415* (2013.01); *A61B 5/0871* (2013.01); *A61B 5/09* (2013.01);
(Continued)

(58) Field of Classification Search
USPC .......................................... 116/147; 446/204
See application file for complete search history.

(56) References Cited

U.S. PATENT DOCUMENTS 3,611,801 A 10/1971 Fagot et al.
3,638,355 A * 2/1972 Stoecklin ............... A63H 33/40
446/216

(Continued)

FOREIGN PATENT DOCUMENTS

EP 0178042 4/1986
WO 95/01552 1/1995

OTHER PUBLICATIONS

Virginia Tech Multimedia Music Dictionary, Acme siren, 2006, Web, Retrieved from:http://www.music.vt.edu/musicdictionary/texta/Acmesiren.html.*

(Continued)

*Primary Examiner* — Jacqueline Cheng
*Assistant Examiner* — Angeline Premraj
(74) *Attorney, Agent, or Firm* — Dorsey & Whitney LLP (57) ABSTRACT

Embodiments of the present invention are directed a system using a microphone and a mobile computer device comprising a transducer through which a user is to exhale or inhale; the transducer is configured and operable to convert the spirometric flow rate into an audible signal having an audio frequency responsive to the spirometric flow rate, wherein the transducer comprises a rotor including a plurality of rotor blades configured to rotate the rotor responsive to a spirometric flow; wherein the microphone is external to the transducer and is adapted to detect the audible signal having the audio frequency and to convert the audible signal to a corresponding electrical signal having the audio frequency.

19 Claims, 6 Drawing Sheets

Related U.S. Application Data (60) Provisional application No. 61/385,166, filed on Sep. 22, 2010.

(52) U.S. Cl.
CPC .......... *A61B 5/6898* (2013.01); *A61B 5/7257* (2013.01); *A61B 5/0022* (2013.01); *A61B 2562/0204* (2013.01)

(56) References Cited

U.S. PATENT DOCUMENTS

| | | | |
|---|---|---|---|
| 3,991,703 A * | 11/1976 | Faust | G10K 7/04 |
| | | | 116/147 |
| 4,244,230 A | 1/1981 | Bauer | |
| 4,282,883 A | 8/1981 | Yerushalmy | |
| 4,291,704 A | 9/1981 | Petty et al. | |
| 5,357,975 A | 10/1994 | Kraemer et al. | |
| 6,058,932 A | 5/2000 | Hughes | |
| 6,171,237 B1 | 1/2001 | Avitall | |
| 6,190,326 B1 | 2/2001 | McKinnon et al. | |
| 6,228,037 B1 | 5/2001 | Derksen | |
| 6,241,683 B1 | 6/2001 | Macklem | |
| 6,314,822 B1 | 11/2001 | Ford | |
| 7,094,208 B2 | 8/2006 | Williams | |
| 9,138,167 B1 | 9/2015 | Leydon | |
| 2002/0124660 A1 | 9/2002 | Drzewiecki | |
| 2002/0124848 A1 | 9/2002 | Sullivan et al. | |
| 2004/0037428 A1 | 2/2004 | Keller | |
| 2004/0200401 A1 * | 10/2004 | Giebeler | G10K 7/04 |
| | | | 116/147 |
| 2007/0239058 A1 | 10/2007 | Krasilchikov et al. | |
| 2008/0281220 A1 | 11/2008 | Sharifpour | |
| 2010/0140211 A1 * | 6/2010 | Becotte | A63F 9/001 |
| | | | 215/386 |

OTHER PUBLICATIONS

The Great Soviet Encyclopedia, "Siren", 1979, Third Edition, Web, Retrieved from: http://encyclopedia2.thefreedictionary.com/Siren.*
"Anaesthetic and respiratory equipment—peak expiratory now meters for the assessment of pulmonary function in spontaneously breathing humans" British Standard BS EN ISO 23747:2007; Published Aug. 31, 2007.
Photographs of "Acme Siren", Prior Art.

* cited by examiner

ACOUSTIC SPIROMETER SYSTEM

CROSS-REFERENCE TO RELATED APPLICATIONS

This application is a continuation-in-part of U.S. application Ser. No. 13/825,146 filed on 20 Mar. 2013, which is a U.S. national stage application of International Application No. PCT/IB2011/054141 filed on 21 Sep. 2011, which claims priority to U.S. Provisional Application No. 61/385,166 filed on 22 Sep. 2010.

TECHNOLOGICAL FIELD

The present disclosure relates to spirometry.

BACKGROUND

Spirometry is a common pulmonary function test for measuring lung function. Specifically, spirometry is the measurement of the amount (volume) and/or speed (flow) of air that is inspired (inhaled) and/or expired (exhaled). Spirometry is an important technique in disease management for bronchial asthma and chronic obstructive pulmonary disease and other respiratory disorders.

The peak expiratory flow (PEF) is an example of a spirometric value being indicative of a person's maximum expiration flow rate. This value is typically measured with a peak flow meter, a small, hand-held device used to monitor a person's ability to breathe out air. The peak flow meter measures the degree of obstruction in the airways.

GENERAL DESCRIPTION

Spirometric monitoring usually requires sophisticated and expensive medical equipment. Such equipment is usually only available at a designated clinic or medical facility and operated by a trained professional. The gap between visits may be several months or more during which there is no monitoring of the patient's pulmonary function. The practitioner may be unaware of lifestyle factors: diet, exercise, monthly rhythms, daily circadian rhythms, introduction of new medications and withdrawal of medications and other factors which may result in a less than ideal treatment. Specifically, concerning Asthma patients, such ongoing routine monitoring is crucial in order to balance and optimize the dosage of the preventive medications (usually steroid based), in order to allow a symptom free life. Moreover, the introduction of telecommunication technologies in the healthcare environment has led to an increased accessibility to healthcare providers, more efficient tasks, processes and a higher overall quality improvement of healthcare services.

There is thus a need to provide a cost effective, user oriented, friendly and mobile spirometric flow rate measurement system which may be used by the patient, anywhere, and at any time, to monitor, store and/or upload spirometric flow rate and/or provide peak flow measurement results to the medical practitioner. It should be noted that hereinafter the term "spirometric flow rate" refers to spirometric values that can be extracted from a spirometric flow rate graph, such as Peak Expiratory Flow (PEF), Forced Expired Volume in one second (FEV1), vital capacity (VC), Forced Expiratory Flow at 25-75%, 50% or 75% of FVC (FEF25-75%, FEF50%, FEF75%), Forced Expiratory Volume during the first 6 seconds (FVC6). Generally, PEF refers to the maximal expiratory flow rate achieved and this occurs very early in the forced expiratory maneuver. FEV1 refers to the volume expired in the first second of maximal expiration after a maximal inspiration and is a useful measure of how quickly full lungs can be emptied. VC is the maximum volume of air which can be exhaled or inspired during either a maximally forced (FVC) or a slow (VC) maneuver. VC is normally equal to FVC unless airflow obstruction is present, in which case VC is usually higher than FVC. It should be understood that, in order to be able to accurately measure the VC, an entire exhale graph should be monitored from the very beginning to the actual end—including the last tenth of seconds in which the airflow is relatively low. FEV1 may also be expressed as a percentage of the VC or FVC (whichever volume is larger) and gives a clinically useful index of airflow limitation. FEF25-75% is the average expired flow over the middle half of the FVC maneuver and is regarded as a more sensitive measure of small airways narrowing than FEV1. FEF50% and FEF75% (forced expiratory flow at 50% or 75% FVC) is the maximal expiratory flow measured at the point where 50% of the FVC has been expired (FEF50%) and after 75% has been expired (FEF75%). Both indices have a wide range of normality but are usually reproducible in a given subject provided the FVC is reproducible. FVC6 is the forced expiratory volume during the first 6 seconds and is a surrogate of the FVC. The FVC6 (and FEV1/FVC6) is of a particular interest since stopping the expiratory maneuver after 6 seconds is less demanding and easier to perform for patients with airflow obstruction and the elderly, yet is similar to conventional FVC and FEV1/FVC for diagnosing and grading airflow obstruction. The special configuration of the transducer according to one or more embodiments of the present invention allows rotor rotation and sound creation in different breathing situations such as from the very beginning to the actual end i.e. including the last tenth of seconds in which the airflow is relatively low and even in the first 6th second of a forced expiratory mode.

According to an aspect of the present disclosure there is provided a system for measuring spirometric flow rate using a microphone and a mobile computer device connected to or integrated with the microphone. The mobile computer device may include a processor and storage. The storage may be operatively connectible, e.g. over a network, to a computer system used by a practitioner. The system has a transducer adapted for converting a spirometric flow rate into an audible signal with an audio frequency characteristic of the spirometric flow rate. The transducer may include a fluidic oscillator, a mechanical siren, a shredded vortex generator or a pressure orifice. The transducer may be mechanically attachable externally to the microphone to optimize audio noise received by the microphone. It should be noted that the external attachment between the transducer to the microphone enables eliminating or lowering the ambient noise, and obtaining a better signal to noise ratio. The audible signal has a characteristic audio frequency responsive to the spirometric flow produced by chopping the spirometric flow between the stator plate and the rotor plate. The chopped air flow can be directed in an optimal way relative to the microphone's location and no relative movements occur during the measurement. The transducer may avoid physical and electrical connection and electromagnetic coupling to the microphone. The microphone may be adapted to detect the audible signal having an audio frequency and to convert the audible signal to a corresponding electrical signal having audio frequency. The audio frequency may be indicative of inter alia a peak expiratory flow rate, and the output result is then indicative of the peak expiratory flow rate.

The system may include a computer readable medium which includes instructions executable by a processor. The instructions may be operable to enable the processor to receive the electrical signal, to process the electrical signal, to derive the characteristic frequency, and to output a result characteristic of the spirometric flow rate responsive to the audio frequency.

The instructions may be configured to schedule spirometric tests responsive to prior spirometric test results. The instructions may include for deriving, from the audio frequency, a signal processing algorithm which may be a fast Fourier transform (FFT), an auto-correlation function, adaptive-additive algorithm, discrete Fourier transform, Bluestein's FFT algorithm, Braun's FFT algorithm, Cooley-Tukey FFT algorithm, Prime-factor FFT algorithm, Rader's FFT algorithm or a fast folding algorithm.

According to an aspect of the present disclosure there is provided a method for measuring spirometric flow rate which uses a mobile computer device. The mobile computer device may include a processor, a memory and a microphone. The method includes transducing spirometric flow rate into an audible signal having an audio frequency characteristic of the spirometric flow rate which may include a full and continuous spirometric graph throughout the exhalation maneuver as elaborated above. The audible signal may be converted to a corresponding electrical signal having the audio frequency. A transducer may be provided to perform the converting. The processor may be enabled to receive the electrical signal, to process the electrical signal to derive the audio frequency and to output the spirometric flow rate responsive to the audio frequency. The method may be characterized by the audible signal being received by using the microphone of the mobile computer device. The microphone may be external to the transducer thereby avoiding a cable and avoiding a wireless interface between the mobile computer device and the transducer. Scheduled spirometric tests may be enabled which are responsive to prior spirometric test results. Uploading of spirometric test results together with time stamp and user selectable parameters to a computer system in use by a practitioner, may be also enabled. The processor may be enabled to record ambient noise. Upon the ambient noise being higher than a threshold, the processor may alert the user to postpone the use of the transducer, e.g. to postpone the exhalation by the user or to use the transducer again after the ambient noise level has decreased below the threshold.

According to another aspect of the present disclosure there is provided a transducer adapted for converting spirometric flow into an audible signal. The transducer has a stator including a stator plate with a plurality of stator openings. A rotor is rotatably connected to the stator. The rotor may include multiple rotor blades configured to rotate the rotor responsive to the spirometric flow. The transducer avoids having a microphone or any other electronics, resulting in a simple, cost effective and durable device. The audible signal is received externally to the transducer while avoiding a cable connection thereto. The audible signal includes an audio frequency responsive to the spirometric flow. The rotor may include a rotor plate with multiple rotor openings. The spirometric flow through the stator openings and the rotor openings occurs substantially only when the stator openings and rotor openings are at least partially aligned. The audible signal has a characteristic audio frequency responsive to the spirometric flow produced by the chopping spirometric flow between the stator plate and the rotor plate. The microphone is external to the transducer and may be adapted to detect the audible signal having an audio frequency and to convert the audible signal to a corresponding electrical signal having the audio frequency.

According to some embodiments of the present invention there is provided an acoustic mechanical transducer configured and operable to continuously transform varying air flow to a varying sound signal. The transducer comprises a stator and a rotor. The rotor is positioned at a proximity to the stator and can be rotated relative to the stator. The rotor comprises an outer ring-shaped part configured for supporting blades and an inner ring-shaped part comprising openings for chopping the air. The stator can comprise two ring-shaped/circle-like portions: an inner ring-shaped part comprising openings for chopping the air, and an outer ring-shaped part in which the air flows freely. The air flow which the user blows into the transducer is divided into two air streams: the major part of the air flows through the blades area of the rotor and the free flow area of the stator (or vice versa) and is responsible for rotating the rotor about its center axis. The other part of relatively smaller air stream, flows through the chopping area of both the stator and the rotor and responsible for creating the chopping sound when rotation occurs. This special arrangement enables to provide an audible varying sound which optimally correlates with the rotational speed of the rotor, which in turn correlates with the intensity of the blow. Furthermore, this arrangement allows an immediate real time response of the audible sound. It should be noted that the term "audible sound" generally refers to sound frequency being indicative of the intensity of the blow, while also allowing the sound frequency to be continuous throughout the entire typical exhalation graph of a user blowing through the device and thereby simulating a typical spirometric exhalation graph.

It should be understood that the special configuration of the transducer according to one or more embodiments of the present invention allows achieving good responsiveness of the rotational speed relative to the air flow. The blades area of the rotor is located in the outer circle in order to produce high rotational moment out of the force applied by the blades (the moment depends on the force multiplied by the radius). Furthermore, the blade matrix is lightweight compared to the chopping area and thus it is preferable to have the blades in the outer circle for lower moment of inertia.

Low moment of inertia is of a particular significance in order to get good responsiveness between the air flow and the rotational speed, thereby achieving a better spirometric graph, including ramp-up and decreasing of the flow.

Moreover, it should be noted that the transducer is configured such that low friction force exists between the rotor and the static parts. This low friction can be achieved by using magnetic bearing, tailstock bearing, sliding bearing, air bearing or ball bearing. The low friction force enables the rotation of the rotor with minimal energy loss, even in low air flow values (such as at the beginning and specifically at the end of a spirometric measurement).

In some embodiments, the inner ring-shaped part of the rotor is configured to be as small as possible relative to the outer ring-shaped part so that most of the air flow flows undisturbed and the pressure drop is as low as possible. A low pressure drop is a significant parameter for spirometric measurement in order to reduce the influence on the measured value and to allow minimal obstruction and resistance to the user's natural exhalation.

In order to make the air flow chopped, alternate openings in the stator and in the rotor are required. The openings can be up to about 50% of the area of the chopping inner ring-shaped part so that the pressure drop on this area is minimal yet sufficient to create an audible sound signal which can be captured by the microphone. It should be understood that a higher openings area (more than 50%) would produce a blurred sound, while lower openings area would increase the pressure drop and also would make the rotor heavier, and thus with higher moment of inertia.

In some embodiments, the mechanical and acoustic structure are optimally tuned to create a low intensity and high frequency audible sound, which is practically undetectable by the human ear, yet can still be captured and analyzed using a sensitive enough microphone (such as in mobile phones). One possible arrangement which allows the above is by minimizing the diameter of the chopping openings/holes and maximizing the number of these holes. Another option which can further be implemented in parallel to the previous one is diverting the vast majority (e.g. 80-99%) of the air stream/flow to a "free-flow" zone while allowing only the minimal remaining air to flow through the chopping holes. This will cause a minimal pressure drop and minimal sound intensity.

In some embodiments, the rotor is made from a high strength and low mass material such as high density polymer, composite material or foamed plastic which combines structural integrity with micro air gaps to optimize the mass/volume ratio, so that the moment of inertia is as low as possible, but the part keeps its rigidity.

In some embodiments, the blades of the rotor are positioned at a certain angle in the range of about 0° to 90° relative to the direction of the air flow. In this way, the blades apply tangential force on the rotor and make it rotate when air flow exists. If the blades would be parallel or perpendicular to the air flow, they would not apply any tangential force.

This unique element in which the rotation part (i.e. the blade) is separated from the chopping part (i.e. the openings) allows an implementation of an optimized aerodynamic blade profile generally similar to a wing in order to maximize the force which is applied to each blade, and thereby the combination of forces which create the moment and rotate the rotor. Furthermore this part allows optimization of the number of blades necessary to assure maximal moment creation throughout the range of relevant airflows which are typical in human exhalation.

According to another embodiment of the present invention, the transducer comprises a second array of static blades configured to transform the air flow from axial to rotational (coil-like). The array includes static inclined and helix blades. In this way a static air tunnel is provided in which the air flows through before hitting the blades area of the rotor. In this embodiment, the first non-static blades of the rotor are parallel to the rotation axis and still produce rotation due to the rotational movement of the air flow.

It should be understood that generally, acoustic sensors measure flow as the primary signal and calculate volume by electronic (analog) or numerical (digital) integration of the flow signal. Commercially available sensors detect and measure flow from at least one of: pressure drop across a resistance (e.g. pneumotach or orifice); cooling of a heated wire (anemometer); electronically counting the rotation of a turbine blade; and time of flight of an ultrasonic sound pulse directed across the expired gas flow (ultrasonic sensor). The transducer according to one or more embodiments of the present invention creates mechanical rotation to produce an audible sound signal which can be recorded in real time on a smart device (smartphone/computer/other) while eliminating counting the number of rotations. The transducer produces a coherent consistent analog acoustic output for each and every flow rate. The acoustic signal provided by the transducer according to one or more embodiments of the present invention is continuous and the acoustic signal follows the flow curve/flow changes in real time and in maximum adherence. In order to produce a full spirogram (i.e. spirometric graph), the system according to one or more embodiments of the present invention provides a flow curve accurately and continuously throughout the exhalation.

According to another aspect of the present disclosure, there is provided a computer readable medium including instructions executable by a mobile computer device. The mobile computer device may include a processor and a microphone for use in a system for measuring a spirometric flow rate. The system may include a transducer adapted to transduce a spirometric flow rate into an audible signal with an audio frequency characteristic of the spirometric flow rate. The microphone receives the audible signal. The microphone is external to the transducer thereby avoiding a cable between the mobile computer device and the transducer. The computer readable medium comprises instructions executable by the processor. The instructions are operable to enable the processor to receive an electrical signal from the microphone responsive to the audio frequency, to process the electrical signal to derive the frequency and to output e.g. display, store and/or transfer over the Internet, the spirometric flow rate responsive to the audio frequency.

BRIEF DESCRIPTION OF THE DRAWINGS

Embodiments of the invention is herein described, in a non-limiting manner, by way of example only, with reference to the accompanying drawings, wherein.

The foregoing and/or other aspects will become apparent from the following detailed description when considered in conjunction with the accompanying drawing figures.

DETAILED DESCRIPTION OF EMBODIMENTS

Reference will now be made in detail to features of the present invention, examples of which are illustrated in the accompanying drawings, wherein like reference numerals refer to like elements throughout. The features are described below to explain the present invention by referring to the figures.

The features of the present invention may comprise a general-purpose or special-purpose computer system including various computer hardware components, which are discussed in greater detail below. Features within the scope of the present invention also include computer-readable media for carrying or having computer-executable instructions, computer-readable instructions, or data structures stored thereon. Such computer-readable media may be any available media, which is accessible by a general-purpose or special-purpose computer system. By way of example, without limitation, such computer-readable media can comprise physical storage media such as RAM, ROM, EPROM, flash disk, CD-ROM or other optical disk storage, magnetic disk storage or other magnetic storage devices, or any other media which can be used to carry or store desired program code means in the form of computer-executable instructions, computer-readable instructions, or data structures and which may be accessed by a general-purpose or special-purpose computer system. Computer-readable media may include a computer program or computer application downloadable to the computer system over a network, such as a wide area network (WAN), e.g. Internet.

In this description and in the following claims, a "computer system" is defined as one or more software modules, one or more hardware modules, or combinations thereof, which work together to perform operations on electronic data. For example, the definition of computer system includes the hardware components of a personal computer, as well as software modules, such as the operating system of the personal computer. The physical layout of the modules is not important. A computer system may include one or more computers coupled via a computer network. Likewise, a computer system may include a single physical device (such as a phone or Personal Digital Assistant "PDA") where internal modules (such as a memory and processor) work together to perform operations on electronic data. While any computer system may be mobile, the term "mobile computer system" or the term "mobile computer device" as used herein especially includes laptop computers, netbook computers, cellular telephones, smart phones, wireless telephones, personal digital assistants, portable computers with touch sensitive screens and the like.

The term "server" as used herein refers to a computer system including a processor, data storage and a network adapter generally configured to provide a service over the computer network. A computer system which receives a service provided by the server may be known as a "client" computer system.

In this description and in the following claims, a "network" is defined as any architecture where two or more computer systems may exchange data. The term "network" may include wide area network, Internet local area network, Intranet, wireless networks such as Wi-Fi™, virtual private networks, mobile access network using access point name (APN) and Internet. Exchanged data may be in the form of electrical signals that are meaningful to the two or more computer systems. When data is transferred or provided over a network or another communications connection (either hardwired, wireless, or a combination of hardwired or wireless) to a computer system or computer device, the connection is properly viewed as a computer-readable medium. Thus, any such connection is properly termed a computer-readable medium. Combinations of the above should also be included within the scope of computer-readable media. Computer-executable instructions comprise, for example, instructions and data which cause a general-purpose computer system or special-purpose computer system to perform a certain function or group of functions.

The articles "a", "an" as used herein, such as "a processor", "a server", "a sample" have the meaning of "one or more" that is "one or more processors", "one or more servers" and "one or more samples".

Before explaining features of the invention in detail, it is to be understood that the invention is not limited in its application to the details of design and the arrangement of the components set forth in the following description or illustrated in the drawings. The invention is capable of other features or of being practiced or carried out in various ways. Also, it is to be understood that the phraseology and terminology employed herein is for the purpose of description and should not be regarded as limiting.

Figure 1A:
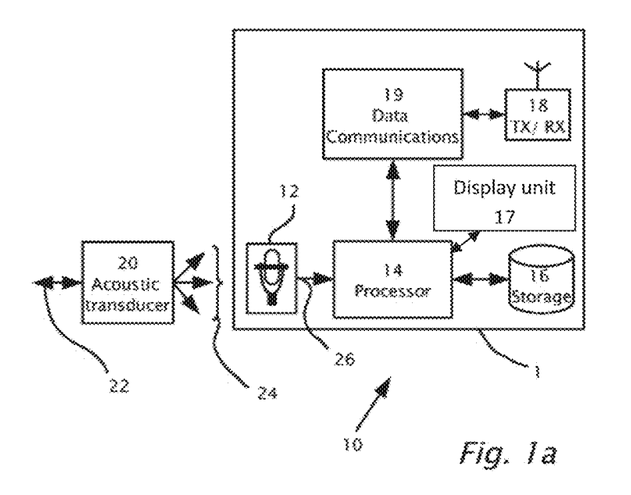
FIG. 1a shows a system diagram for measuring spirometric flow rate using an acoustic transducer and a mobile computer device, according to an exemplary feature of the present invention.

Referring now to the drawings, FIG. 1a shows a system 10 for measuring spirometric flow rate and/or other spirometric values using a microphone 12 and a mobile computer device 1 connected to or integrated with microphone 12 and including a processor 14, according to an exemplary feature of the present invention. The system 10 comprises an acoustic transducer 20 through which a user is to exhale or inhale, and a non-transitory computer readable medium 16 including instructions executable by processor 14, wherein the instructions, when executed, cause processor 14 to receive the corresponding electrical signal, to process the corresponding electrical signal, to derive the audio frequency and to output as a result the spirometric flow rate responsive to the audio frequency. Transducer 20 is configured and operable to convert a spirometric flow rate into an audible signal 24 having an audio frequency responsive to the spirometric flow rate. Microphone 12 is external to transducer 20 and is adapted to detect the audible signal having the audio frequency and to convert the audible signal to a corresponding electrical signal having the audio frequency. Transducer 20 comprises a rotor including a plurality (i.e. one or more) of rotor blades configured to rotate the rotor responsive to a spirometric flow as will be detailed below with respect to FIG. 2a. A user exhales and/or inhales through acoustic transducer 20 to undergo spirometric monitoring. Acoustic transducer 20 converts spirometric flow rate into an audible signal 24. An example of acoustic transducer 20 may be based on known designs such as a fluidic oscillator described in U.S. Pat. No. 4,244,230 in which a feedback loop creates vibrations at a frequency that is a function of pressure or flow rate. Audible sound signal 24 with a frequency range from 100 Hz to 32 KHz from transducer 20 may be optimal for microphone 12 at typical flow rates of 50 to 800 liters per minute.

Another example of acoustic transducer 20 may be in which air flow produces a shredded vortex in a frequency that is proportional to flow rate. The generated audible sound signal 24 from the shredded vortex may not be very strong when compared to other acoustic devices and may also have a broader spectrum of audio frequencies.

Another example of acoustic transducer 20 may be based on an electronic acoustic device based on any kind of flow meter that has electronic output that modulates an acoustic frequency generator having a monotonous characteristic of flow rate (50-800 l/min) vs. frequency the range of 50 to 3000 Hz. Optionally the acoustic transducer 20 may produce a different frequency range for inspiration and expiration. The flow meter may include for instance an orifice plate placed in the path of airflow. An orifice plate is a device used for measuring the volumetric flow rate. It uses the same principle as a Venturi nozzle, namely Bernoulli's principle which states that there is a relationship between the pressure of the air and the velocity of the air. When the velocity increases, the pressure decreases and vice versa. From a sensed difference in air pressure before the orifice plate and after the orifice plate, the volumetric and mass flow rates may be obtained from Bernoulli's equation. For transducer 20, audible sound signal 24 generation may be performed by a microprocessor with an analog input of the sensed difference at the orifice which generates audible sound signal 24 corresponding to the sensed difference.

A possible standard to follow and apply with respect to spirometer design may be British standard BS EN ISO 23747-2009. British standard BS EN ISO 23747-2009 entitled "*Anaesthetic and respiratory equipment. Peak expiratory flow meters for the assessment of pulmonary function in spontaneously breathing humans*" deals with Anaesthetic equipment, Flow meters, Anaesthesiology, Medical breathing apparatus, Electrical medical equipment, Medical equipment, Respiratory system, Flow measurement, Measuring instruments, Safety devices and Performance.

Referring back to FIG. 1a and system 10, computer device 1 may include and have connected thereto a display unit 17, data communications 19, a cellular telephone transceiver (not shown) and/or data transceiver 18. Microphone 12 may be located internally within device 1, on the external surface of device 1, or externally connected to mobile computer device 1 through an audio input. Microphone 12 is operable to detect audible signal 24 having an audio frequency responsive to the spirometric flow. Processor 14 is operable to receive an analog or digitized electrical signal 26 responsive to the spirometric flow rate and based on the frequency of audible signal 24 outputs a spirometric flow rate and optionally stores the flow rate as data in storage 16.

Processor 14 may include sample and hold circuitry and analog-to-digital converters (ADC) for converting audio electrical signal 26 to a corresponding digital signal. Storage 16 may store signal processing algorithms used by processor 14 for a signal processing of audio electrical signal 26. Results of the signal processing function of audio electrical signal 26 may be stored in storage 16 displayed or transferred to data communications 19.

The use of transducer 20 which outputs an acoustic signal avoids the requirement of a cable between mobile device 1 and transducer 20. Moreover, the use of radio frequency RF transceivers or wireless interface such as Bluetooth™ may also be avoided, according to features of the present invention.

Figure 1B:
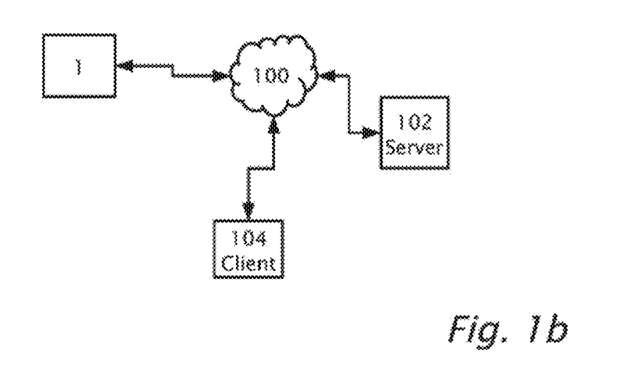
FIG. 1b shows a wide area network (WAN) bi-directionally connectible to a mobile computer device, a server and a client.

Reference is now also made to FIG. 1b which shows a wide area network (WAN) 100 bi-directionally connectible to mobile computer device 1, a server 102 and a client 104. Server 102 may provide the exchange of information between client 104 and mobile computer device 1. Client 104 may belong to a practitioner including medical personnel e.g. pulmonologist, nurse.

Figures 2A, 2B:
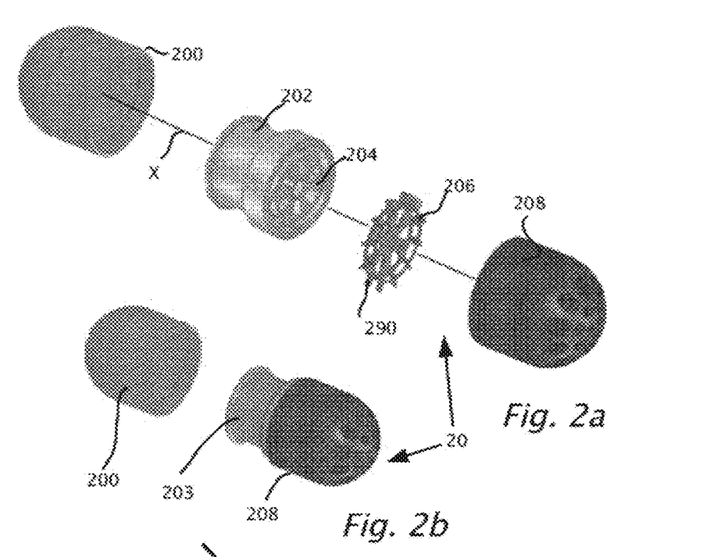
FIGS. 2a, 2b and 2c show feature details and usage of an example of acoustic transducer based on a mechanical siren.
Figure 2C:
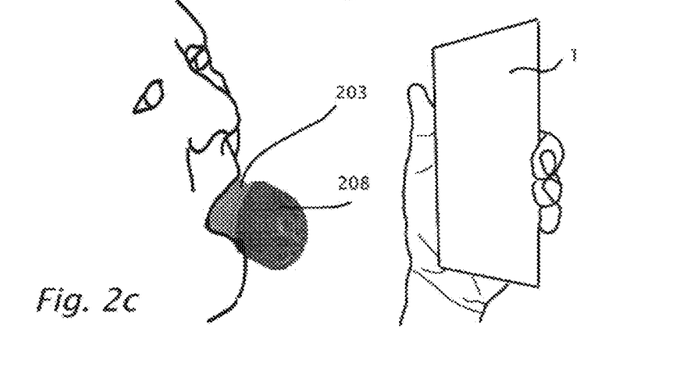

Reference is now made to FIGS. 2a, 2b and 2c which feature details and usage of an example of acoustic transducer 20 based on a mechanical siren. FIG. 2a is an exploded partial view of FIG. 2b. In this specific and non-limiting example, transducer 20 includes a stator 202 having a stator plate 204 including openings, a rotor 206 rotatably connected to stator 202 and having rotor blades and openings. Optionally the transducer 20 may include a vent 208 including openings and a protective cap 200. A spindle may be located in the center of stator plate 204 and be attached to the center of rotor 206 to allow rotation of rotor 206 about axis X. Rotation of rotor 206 occurs when the user exhales and/or inhales through the mouthpiece 203 sealed inside the mouth of the user during spirometric testing. As illustrated in FIG. 2a, the plurality of rotor blades is mounted on an external ring-shaped part, and the plurality of rotor chopping openings is mounted on an internal ring-shaped part. The air flow is therefore divided to those two circles into internal and external flows respectively. The internal flow goes through chopping and produces the sound signal, and the external flow makes the rotor 206 rotate. It should be noted that this special configuration of the rotor according to at least one embodiment of the present invention provides a low/minimal mechanical inertia of the rotor. This configuration enables the rotor to have a low inertia, and by that to be responsive to the air flow, in order to make the spirometric measurement possible and accurate. This configuration also enables allowing low pressure drop on the internal chopping circle.

When spirometric air flow enters acoustic transducer 20, the air flows through the rotor blades which cause rotor 206 to rotate. Rotation of rotor 206 causes audible signal 24 to emanate from acoustic transducer 20 as spirometric air flows through mouthpiece aperture (not shown), through openings in stator plate 204, openings in rotor 206 and optionally openings in vent 208. Stator plate 204 may have a number of slots or openings which may be similar in size and shape to the slots or openings of rotor plate of rotor 206. As rotor 206 rotates, audible signal 24 is produced by the chopping and consequent pressure variation of spirometric flow between the stator plate 204 and the rotor plate of rotor 206. When the openings in both plates are at least partially aligned, air flows through the openings, and when the openings are not aligned, the air flow is blocked. The transformation between open and blocked openings creates the chopping action. The chopped air flow and pressure in the consequent variation create audible signal 24, the frequency of which may depend on the rotational speed of the rotor 206. Higher rotational speed causes higher sound frequency. Consequently, an audio electrical signal 26 with a characteristic audio frequency responsive to the spirometric flow rate is produced by the chopping. Cap 200 of FIG. 2a may be used to protect mouthpiece 203 when transducer 20 is not being used. Cap 200 may also not be used at all.

Figure 2D:
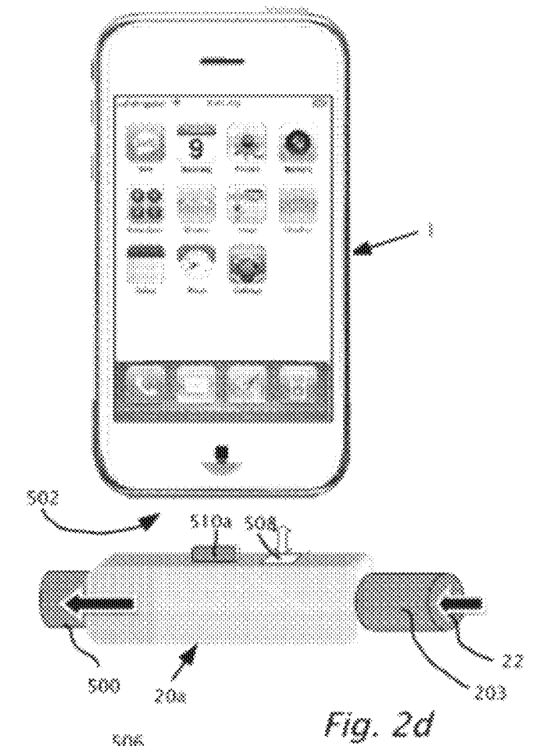
FIG. 2d shows an exemplary feature of an acoustic transducer.
Figure 2E:
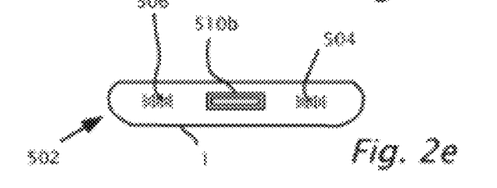
FIG. 2e shows a bottom view of a mobile computing device to be used with the transducer of FIG. 2d.

Audible signal 24 may be received by microphone 12 of mobile computer device 1. Mobile computer device 1 may be held in the vicinity of transducer 20 by the hand of the user as shown in FIG. 2c. Reference is now made to FIG. 2d which shows an exemplary feature of another configuration of an acoustic transducer 20a. The acoustic transducer 20a has mouthpiece 203 which is placed in the mouth of a user. The user exhales and/or inhales to cause a spirometric air flow 22 through acoustic transducer 20a. Flow 22 continues through tube 500 on the opposite side to mouthpiece 203. FIG. 2e shows a bottom view 502 of a mobile computing device 1 to be used with a transducer of FIG. 2d. The bottom 502 of mobile computing device 1 has two openings defined by apertures 506 and 504 in a speaker (not shown) and microphone 12 (not shown) of device 1 are located respectively. Bottom 502 may also have a female docking port 510b. Before exhaling and/or inhaling into mouthpiece 202, transducer 20a may be mated with device 1 by inserting male docking port 510a of transducer 20a into female docking port 510b of device 1. Inserting male docking port 510a into female docking port 510b also aligns aperture 508 of transducer 20a with aperture 504, where built-in microphone of device 1 is located. Inserting male docking port 510a into female docking port 510b followed by use of transducer 20a by the user may allow for non interference of unwanted noise or sound external to transducer 20a and device 1. A fixed distance between audible signal 24 and microphone may be achieved by use of transducer 20a mated with device 1.

Figure 3A:
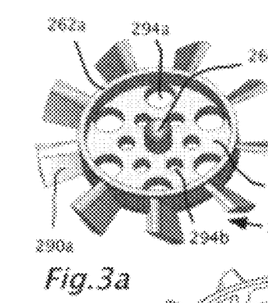
FIGS. 3a, 3b and 3c show a number of further examples for a rotor.
Figure 3B:
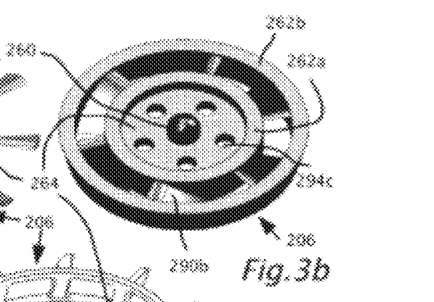
Figure 3C:
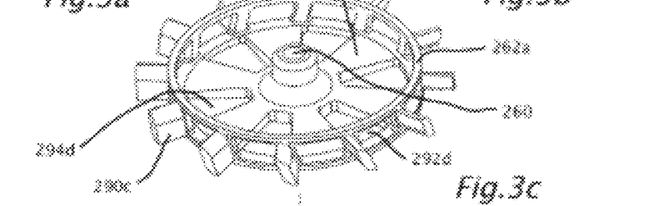

Reference is now made to FIGS. 3a, 3b and 3c which show a number of further examples of rotor 206. Different features for rotor 206 may produce different sound characteristics for audible signal 24 when rotor 206 is rotated. Common to rotors 206 in FIGS. 3a, 3b and 3c are blades 290a, 290b, 290c respectively, spindle housing 260, blade housing 262a and rotor plate 264. Blades 290a, 290b, 290c are configured to exert a rotational force on rotor 206 when spirometric air flows through transducer 20. In some embodiments illustrated in FIG. 3a, the rotor plate 264 has a plurality of holes arranged in a ring-shaped manner, each ring being of a different diameter. One ring may thus be configured for free flow and the other one for chopping. In the figure, the rotor plate 264 has larger circular openings 294a through the outer circumference of plate 264 and smaller circular openings 294b through the inner circumference of plate 264. The diameter of the chopping holes may be reduced to minimal.

Rotor plate 264 in FIG. 3b has circular openings 294c through the outer circumference of plate 264. Plate 264 in FIG. 3c has trapezoidal openings/slots 294d which extend from the inner circumference to the outer circumference of plate 264. Blades 290a, 290b and 290c attach and protrude outwards from their respective blade housings 262a. In the configuration of FIG. 3b, the ends of blades 290b are additionally attached to an outer blade housing 262b. In the configuration of FIG. 3c, the blade housing 262a also has additional slots 292d between blades 290c.

Figure 3D:
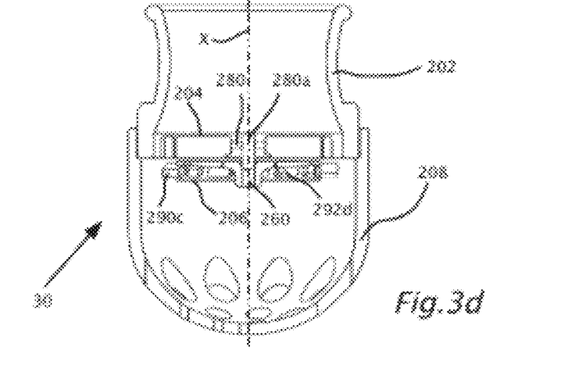
FIG. 3d shows a cross sectional plan view along an axis of a stator which includes a stator plate and a rotor.

Reference is now made to FIG. 3d which shows a cross sectional plan view 30 along axis X of rotor 206 and vent 208 and stator 202 which includes stator plate 204 of FIG. 2a. In view 30, stator plate 204 is mounted at right angles to stator's axis X. Stator 202 includes a spindle 280a which runs along axis X. Spindle 280a is attached at one end to rotor housing 260 and the other end of spindle 280a located and attached in bearing 280. Bearing 280 allows the rotation of rotor 206 about axis X. Alternatively, bearing 280 may be located in rotor housing 260 and spindle 280a fixed at right angles to stator's axis X.

Rotor 206 and stator 202 may be configured so that the highest frequency of the sound signal at maximal spirometric flow is not noisy or disturbing to the user or to others. The lowest frequency should be high enough to be sensed by the microphone.

For calculating the rotational speed of rotor 206, the air flow speed may be calculated in a first section (rotor blades section) which is proportional to a volumetric flow rate of the respiration. The volumetric flow rate is the percentage of the air which goes to the first section and the cross section area of the flow in the first section. The rotational speed may be proportional to the air flow speed in the rotor blades section and may depend on the angle and form of the rotor blades 290 of rotor 206.

The spirometer may measure a wide range of flow between 50 liters/min to 800 liters/minute. This wide range may be divided to provide a system suitable for children and a system suitable for adults. The system suitable for children may have a lower flow range L1, and for adults a higher flow range L2.

The resistance pressure of the peak flow/spirometer has to be lower than 1.5 cm of water per 1 liter per second (for example for flow of 10 liters per second, the resistance pressure should be less than 15 cm of water).

The peak flow may measure transient peak flow during 0.1 second, and therefore the transducer preferably reaches a typical flow within 0.05 second.

Since the measurement of the spirometric flow may be performed by handset with built in microphone, a transducer may produce frequency and intensity that can be detected by the handset and microphone that is not attached to transducer. The following parameters may be suggested:

At low flow L1, the transducer's frequency may be more than 30 Hz, (100 Hz may be optimal), as the microphone may be less sensitive to lower frequencies, while the resistance pressure of the peak flow/spirometer may be over 0.2 cm of water in order to produce a detectable audible sound signal at low frequency.

At high flow rates L2, transducer's basic frequency (first harmonic) may be less than 18 KHz, as the microphone may not be sensitive above 18 KHz. The system may be configured to provide a highest frequency of 3 KHz to decrease acceleration requirements for rotor and reliability concerns.

Pressure drop can be estimated by a flow cross section A (not shown) i.e. the area of the openings through which the air flows and a flow rate using well known Bernoulli formula as a first approximation. Cross section A may be calculated from range L2 pressure limits or using 1.5 cm of water per 1 liter per minute.

The basic frequency equals to rotor revolutions per second multiplied by the number of the openings in the rotor. The preferred number of openings may be 6 to 10. More openings may not be effective as a chopper. Fewer openings may require increasing the rotor speed and may require higher acceleration.

Transducer basic frequency (first harmonic) rotor frequency may be calculated by the angle of rotor blades using known methods.

The number of blades and profile of blades may be optimized to supply the required torque that is required to provide acceleration requirements of reaching the maximal flow at 0.05 seconds.

In some embodiments, the rotor is constructed with minimal moment of inertia, using low density and high strength polymers, for example polycarbonate.

Figure 3E:
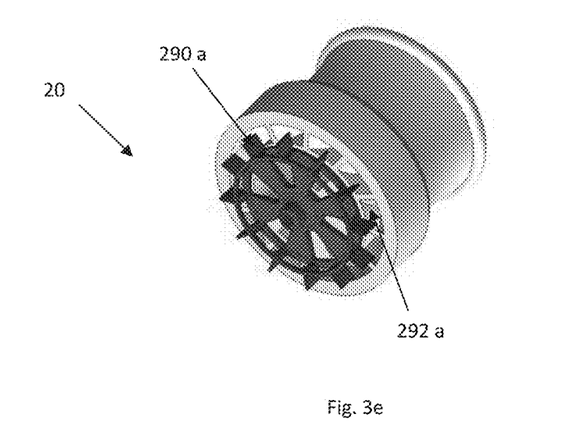
FIG. 3e shows another possible configuration of the transducer.
Figure 3F:
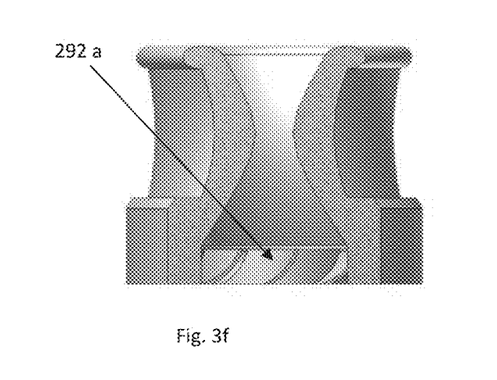
FIG. 3f shows a partial cross sectional view of the transducer of FIG. 3e.

Reference is made now to FIGS. 3e-3f illustrating another embodiment of the present invention, in which the transducer 20 comprises a second array of static blades 292a configured to transform the air flow from axial to rotational (coil-like). FIG. 3f illustrates a cross section of a partial part of the transducer having an array of static inclined and helix blades 292a. In this way, a static air tunnel is provided in which the air flows through before hitting the blades area of the rotor. In this embodiment, the first non-static blades of the rotor 290a are parallel to the rotation axis and still produce rotation due to the rotational movement of the air flow.

Figure 4:
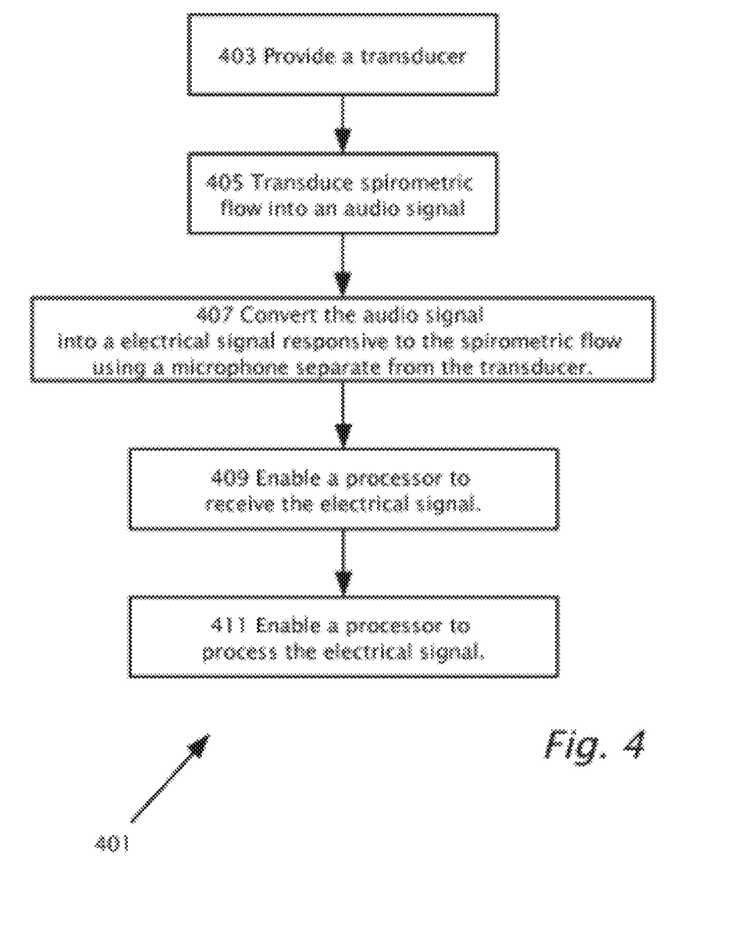
FIG. 4 shows a method which may be used to measure spirometric flow rate using an acoustic transducer and a mobile computer device, according to an exemplary feature.

Reference is now made to FIG. 4 which shows a method 401 which may be used to measure spirometric flow rate using acoustic transducer and mobile computer device, according to an exemplary feature. In step 403 a transducer is provided. The user inserts a mouthpiece into the mouth. The user exhales and/or inhales which causes spirometric air flow through the acoustic transducer. Airflow causes the rotor to rotate which transduces the spirometric air flow to give an audible signal in step 405. The audible signal is then converted into an electrical signal by a microphone in step 407. An electrical signal may be responsive to the spirometric air flow through the acoustic transducer. A processor may include sample and hold circuitry, analog to digital converters (ADC), digital to analog converters (DAC) and some working memory which enables the processor to receive an electrical signal in step 409. After the electrical signal is received, the processor is also enabled to process the electrical signal in step 411. Processing of signal in step 411 may be implemented by signal processing algorithms known in the art of signal processing. Results of signal processing step 411 may be displayed and/or stored in storage and/or sent to data communication unit for transfer over a wide area network, e.g. Internet.

Initialization of the system may include entering data such as age, sex, target respiration values, alert thresholds and medication schedules. Initialization may be performed by the user himself or by a practitioner located at a distant client or server as illustrated in FIG. 1b. The system according to one or more embodiments of the present invention may usually be in a stand-by mode until the user chooses the spirometer measurement option, or the stand-by mode may be entered by instructions via communication channels.

In a measurement mode operation, the system according to one or more embodiments of the present invention may provide notification for a start of a measurement. During the measurement, the system according to one or more embodiments of the present invention may record the characteristic frequency of the acoustic transducer. The sound recording, sound analysis and frequency detection of the audible sound signal may be performed in real time on small time frames of, for example, 0.1 seconds in order to detect the sound signal. The signal analysis may be performed by a Fast Fourier Transform (FFT) to detect the maximum power at a particular frequency. The FFT may be performed in a defined frequency range e.g. 100-2000 Hz for an acoustic transducer held at a distance away from the mobile device by a user. Since environmental noises may interfere with the measurement, a noise rejection procedure may be suggested to avoid artifacts. The system according to one or more embodiments of the present invention may use noise rejection criteria having a characteristic transducer frequency (for example local maxima of the frequency in the range of 100-3000 Hz) 3 to 4 times the surrounding environmental root mean squared (RMS) audio noise. In case the particular (characteristic) frequency is not detected within 5-10 seconds, an error message may be presented and the user can start over the recording or close the application and the system according to one or more embodiments according to one or more embodiments according to one or more embodiments according to one or more embodiments according to one or more embodiments of the present invention goes into the stand-by mode.

The flow rate calculation may be performed in real time by software installed in the mobile computer device (or on the cloud/server) or after the recording session. The recording session ends 5-10 seconds after the particular frequency detection or when the characteristic frequency is not detected. After the recording session is over, the flow rate may be calculated by using calibration data (from a function or a look-up table) of frequency versus flow rate. Additional respiratory parameters calculated from the flow rate curve as a function of time may be saved with a time stamp and optionally transferred to web-service management center, e.g. server illustrated in FIG. 1b.

An analysis of the respiratory parameters may include comparing the respiratory parameters to predefined values, and in case of deviation from the normal values an alert may be presented to the user, with recommendations. The analysis may be performed in software of the mobile computer device or in a facility that is supervised by a clinician. Device software and web servers' software may work as one system, which may enable cost-effective supervision by the clinician and access of data by authorized users for disease management.

A scheduling of measurement may be performed by fixed schedule or by an adaptive regime. Fixed scheduling may be performed by programming time intervals between scheduled measurements or a time to measure, as indicated to the user. Adaptive scheduling may be based on the trending information and scheduled intervals. While the measured respiratory values are in a normal range, a measurement may be performed at pre-scheduled intervals. When the measured spirometric measurement results are not normal, the measurement intervals may be decreased according to a pre-defined logic.

The application installable on the mobile computer device may enable the entering of user selectable parameters and/or treatment parameters that can be correlated to the respiratory measurement results and displayed on the same chart, or uploaded to the practitioner, for example. User selectable parameters may include: lifestyle factors: diet, exercise, monthly rhythms, daily circadian rhythms, introduction of new medications and withdrawal of medications. A user selectable parameter that may be correlated over a time period of spirometric measurements of respiratory parameters for asthma, for example, may be movement, e.g. aerobic exercise, of a user using over the time period using a mobile computer device which includes a built-in acceleration sensor. The system according to one or more embodiments of the present invention can therefore be configured to present and display combined charts of breathing parameters with other measurable or manually entered parameters.

Although selected features of the present invention have been shown and described, it is to be understood the present invention is not limited to the described features. Instead, it is to be appreciated that changes may be made to these features without departing from the principles and spirit of the invention, the scope of which is defined by the claims and the equivalents thereof.

The invention claimed is:

1. A system using a microphone and a mobile computer device connected to or integrated with the microphone, wherein the mobile computer device includes a processor, the system comprising:
   a transducer through which a user is to exhale or inhale; said transducer being configured and operable to convert a spirometric flow rate into an audible signal having an audio frequency responsive to the spirometric flow rate, wherein said transducer comprises a rotor comprising a rotor body including a plurality of rotor blades configured to rotate said rotor responsive to a spirometric flow; the rotor body defining a plurality of rotor chopping openings disposed between the plurality of rotor blades; and a ring-shaped part from which the plurality of rotor blades project; wherein the microphone is external to said transducer and is adapted to detect said audible signal having said audio frequency and to convert said audible signal to a corresponding electrical signal having the audio frequency; and
   a non-transitory computer readable medium including instructions executable by the processor, wherein said instructions, when executed, cause the processor to receive said corresponding electrical signal, to process the corresponding electrical signal, to derive said audio frequency and to output as a result the spirometric flow rate responsive to said audio frequency.

2. The system of claim 1, wherein said transducer comprises a stator including a stator plate with a plurality of stator openings, wherein said stator is rotatably connected to said rotor.

3. The system of claim 1, wherein said transducer is mechanically attachable externally to said microphone.

4. The system of claim 1, wherein said audio frequency is indicative of a peak expiratory flow rate and said result is thereby indicative of the peak expiratory flow rate.

5. The system of claim 1, wherein said audio frequency depends on a rotational speed of said rotor.

6. The system of claim 1, wherein said non-transitory computer readable medium is configured and operable to perform a signal processing for deriving said audio frequency, said signal processing comprising at least one of: a fast Fourier transform (FFT), an auto-correlation function, adaptive-additive algorithm, discrete Fourier transform, Bluestein's FFT processing, Bruun's FFT processing, Cooley-Tukey FFT processing, Prime-factor FFT processing, Rader's FFT processing, or a fast folding processing.

7. A transducer, comprising:
a rotor comprising a rotor body including: a plurality of rotor blades configured to rotate said rotor in response to a spirometric flow, the rotor body defining a plurality of rotor chopping openings disposed between the plurality of rotor blades; and a ring-shaped part from which the plurality of rotor blades project; and a stator rotatably connected to said rotor, said stator comprising a stator body including an inner circle-shaped part comprising openings for chopping the air, and an outer ring-shaped part in which the air flows freely, wherein said transducer is configured and operable for converting a spirometric flow rate into an audible signal having an audio frequency responsive to the spirometric flow rate.

8. The transducer of claim 7, being mechanically attachable externally to a microphone.

9. The transducer of claim 7, wherein said audio frequency is indicative of a peak expiratory flow rate.

10. The transducer of claim 7, wherein said audio frequency depends on a rotational speed of said rotor.

11. The transducer of claim 7, wherein said audible signal has a characteristic audio frequency being produced by chopping spirometric flow between said stator body and said rotor body.

12. The transducer of claim 7, wherein said ring shaped part comprises an external ring-shaped part and an internal ring-shaped part defining the plurality of rotor chopping openings, the plurality of rotor blades extending radially between the internal and external ring-shaped parts.

13. The transducer of claim 7, wherein said rotor body comprises a first and second plurality of rotor openings having a different diameter.

14. The transducer of claim 7, further comprising a blade housing having openings between said blades.

15. The transducer of claim 7, wherein at least one of said plurality of stator and rotor chopping openings have an area up to 50% of the area of the ring-shaped part.

16. The transducer of claim 7, wherein the blades of the rotor are positioned at a certain angle in the range of 0° to 90° relative to a direction of the spirometric air flow.

17. The transducer of claim 7, further comprising a second array of blades having inclined and helix configuration to transform air flow from axial to rotational.

18. The transducer of claim 17, wherein said plurality of blades is positioned parallel to a rotation axis of the rotor.

19. The transducer of claim 7, wherein said rotor body comprises a rotor plate and said stator body comprises a stator plate.

* * * * *